United States Patent
Stoddard

(10) Patent No.: US 11,432,538 B1
(45) Date of Patent: Sep. 6, 2022

(54) BLOOD-FEEDING SYSTEMS AND METHODS FOR HEMATOPHAGOUS ARTHROPODS

(71) Applicant: Philip K. Stoddard, South Miami, FL (US)

(72) Inventor: Philip K. Stoddard, South Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/308,382

(22) Filed: May 5, 2021

(51) Int. Cl.
*B33Y 80/00* (2015.01)
*A23K 10/24* (2016.01)
*A01K 67/033* (2006.01)
*A23K 50/90* (2016.01)

(52) U.S. Cl.
CPC ............ *A01K 67/033* (2013.01); *A23K 10/24* (2016.05); *A23K 50/90* (2016.05); *B33Y 80/00* (2014.12); *A01K 2227/706* (2013.01)

(58) Field of Classification Search
CPC ............ A01K 67/033; A01K 2227/706; A23K 10/24; A23K 50/90; B33Y 80/00
See application file for complete search history.

(56) References Cited

U.S. PATENT DOCUMENTS

| | | | | |
|---|---|---|---|---|
| 5,030,202 A | * | 7/1991 | Harris | A61D 7/00 604/27 |
| 2007/0128715 A1 | * | 6/2007 | Vukasinovic | C12M 23/22 435/303.1 |
| 2008/0249530 A1 | * | 10/2008 | Truckai | A61B 17/8836 606/92 |
| 2011/0319813 A1 | * | 12/2011 | Kamen | A61M 5/1684 604/151 |
| 2015/0342177 A1 | * | 12/2015 | Hassan | A01N 1/0247 435/284.1 |
| 2016/0186240 A1 | * | 6/2016 | Andreyev | B01L 7/525 435/287.2 |
| 2017/0189597 A1 | * | 7/2017 | Caluya | H02S 10/10 |
| 2018/0369470 A1 | * | 12/2018 | Garvey | B01D 19/001 |
| 2019/0111436 A1 | * | 4/2019 | Wescott | B01L 3/502 |
| 2019/0314586 A1 | * | 10/2019 | Minskoff | A61M 15/0066 |

OTHER PUBLICATIONS

Deng et al., A novel mosquito feeding system for routine blood-feeding of Aedes aegypti and Aedes albopictus, Tropical Biomedicine 29(1): 169-174 (2012).

(Continued)

*Primary Examiner* — Rick K Chang
(74) *Attorney, Agent, or Firm* — Saliwanchik, Lloyd & Eisenschenk

(57) ABSTRACT

Blood-feeding systems for hematophagous arthropods, as well as methods of fabricating and using the same, are provided. The blood-feeding systems can be fabricated on site (e.g., in a lab) by using a three-dimensional (3D) printer (e.g., a direct drive 3D printer such as a direct drive fused deposition modeling (FDM)-type 3D printer) and regular lab tools. The blood-feeding systems can utilize a syringe filling system that allows leftover blood to be recovered after use, or added or changed while the feeder is in use.

20 Claims, 4 Drawing Sheets

(56) References Cited

OTHER PUBLICATIONS

Dhar et al., Development of a cheap and simple artificial feeding device for studying dengue virus transmission in Aedes aegypti mosquito at the resource-poor setups, International Journal of Mosquito Research 2019; 6(5): 57-62.

Finlayson et al., A simple and affordable membrane-feeding method for Aedes aegpyti and Anopheles minimus (Diptera: Culicidae), Acta Tropica 152 (2015) 245-251.

Nijhof et al., In vitro Feeding Methods for Hematophagous Arthropods and Their Application in Drug Discovery, Ectoparasites: Drug Discovery Against Moving Targets, First Edition, 2018, 187-204.

Luo, A novel multiple membrane blood-feeding system for investigating and maintaining Aedes aegypti and Aedes albopictus mosquitoes, Journal of Vector Ecology, vol. 39, No. 2, 271-277.

Romano et al., Artificial blood feeders for mosquitoes and ticks—Where from, where to? Acta Tropica 183 (2018) 43-56.

Siria et al., Evaluation of a simple polytetrafluoroethylene (PTFE)-based membrane for blood-feeding of malaria and dengue fever vectors in the laboratory, Parasites & Vectors (2018) 11:236, 10 pages.

Witmer et al., An inexpensive open source 3D-printed membrane feeder for human malaria transmission studies, Malaria Journal (2018) 17:282; 7 pages.

\* cited by examiner

BLOOD-FEEDING SYSTEMS AND METHODS FOR HEMATOPHAGOUS ARTHROPODS

BACKGROUND

Hematophagous (blood-sucking) arthropods studied in the laboratory must be fed warm blood. Many blood feeder designs exist, ranging from a simple sausage casing filled with warmed defibrinated blood, to expensive systems involving blown-glass, water pumps, and/or electric heaters. The blood-filled sausage casing is portable, but it does not maintain temperature. Existing heated systems are attached to a temperature-regulating base station by hoses or electric cables, and are therefore not portable.

BRIEF SUMMARY

There is a need in the art for a reliable and inexpensive blood-feeding system for hematophagous arthropods. Such a feeder should be fully self-contained with its own heat supply and inexpensive to purchase or fabricate. Embodiments of the subject invention provide novel and advantageous blood-feeding systems for hematophagous arthropods, as well as methods of fabricating and using the same. The blood-feeding systems are low-cost, portable, thermally stable, and have superior blood-handling features. They can be fabricated on site (e.g., in a lab), for example by using a three-dimensional (3D) printer (e.g., a direct drive 3D printer such as a direct drive fused deposition modeling (FDM)-type 3D printer) and regular lab tools. The blood-feeding systems are the first fully portable blood-feeders that stay warm for extended periods. The systems can utilize a syringe filling system that allows leftover blood to be recovered after use, or added or changed while the feeder is in use.

In an embodiment, a blood-feeding system for hematophagous arthropods can comprise: a housing comprising a lower block having an opening in an upper surface thereof, an upper block disposed in the opening of the lower block, and a block, which transfers heat from a battery-operated heater to the blood (can be referred to as a "thermal block"), disposed on or in the upper block; the battery-operated heater disposed in the lower block; a ring disposed on the thermal block; a first syringe connected to the ring via a first tubing, the first syringe configured to provide blood to the ring via the first tubing; and a membrane disposed on the thermal block. The ring can comprise serpentine pathways through which the first tubing is threaded. The system can further comprise at least one end clip disposed on a corner of an outer surface of the lower block, the at least one end clip comprising a C-shaped clip into which the first syringe is disposed. The system can further comprise at least one O-ring coupled with the ring and making a seal between the ring and the membrane. The battery-operated heater can be, for example, an electronic hand-warmer. The system can further comprise a second syringe connected to the ring via a second tubing, the second syringe configured to remove air from the ring via the second tubing. The system can further comprise a first end clip disposed on a first corner of an outer surface of the lower block and a second end clip disposed on a second corner (e.g., opposite from the first corner) of the outer surface of the lower block, the first end clip comprising a first C-shaped clip into which the first syringe is disposed, and the second end clip comprising a second C-shaped clip into which the second syringe is disposed. The first syringe can comprise a first blunt hypodermic needle, via which the first syringe is coupled to the first tubing, and/or the second syringe can comprise a second blunt hypodermic needle, via which the second syringe is coupled to the second tubing. The housing can comprise a 3D-printed thermochromic material that changes color as its temperature changes. The upper block can completely close off the opening in the upper surface of the lower block; the thermal block can comprise a cylindrically-shaped main portion and a collar portion protruding from a lower section of the main portion; the main portion of the thermal block can be disposed through an opening of the upper block; and/or the ring can be disposed circumferentially around the main portion of the thermal block. The thermal block can conduct heat from the battery-operated heater to the blood (e.g., to a lower surface of the blood pool). The housing can be unattached (not attached) to any other heating device or power source (e.g., by means of a fluid-carrying tube or electric cable). That is, the housing can be in a state such that it is no attached in any way to any heating device other than the battery-powered heater. The battery-powered heater can be in direct physical contact with the thermal block (e.g., can firmly contact the thermal block).

In another embodiment, a method of providing blood to feed hematophagous arthropods can comprise: providing a blood-feeding system as described herein; turning on the battery-operated heater and allowing the housing to reach a predetermined temperature; filling the first syringe at least partially with the blood; pushing a first plunger of the first syringe to provide blood to the ring via the first tubing; and placing the blood-feeding system with the blood provided to the ring on a container having the hematophagous arthropods. The housing can comprise a 3D-printed thermochromic material that changes color as its temperature changes, and the method can further comprise monitoring a temperature of the housing based on the color of the 3D-printed thermochromic material. The system can further comprise a second syringe connected to the ring via a second tubing, the second syringe configured to remove air from the ring via the second tubing; and the method can further comprise, prior to placing the blood-feeding system with the blood provided to the ring on the container, pulling a second plunger of the second syringe to remove air from the ring via the second tubing.

In another embodiment, a method of fabricating a blood-feeding system for hematophagous arthropods can comprise: utilizing a 3D printer to print a housing comprising a lower block having an opening in an upper surface thereof, an upper block configured to be disposed in the opening of the lower block, and a thermal block configured to be disposed on or in the upper block; utilizing the 3D printer to print a ring comprising serpentine pathways therewithin; disposing a battery-operated heater in the lower block of the housing through the opening of the lower block; providing a first syringe and disposing a first needle on the first syringe; coupling the first needle to a first end of a first tubing, and coupling a second end of the first tubing to the serpentine pathways of the ring; disposing a membrane over the ring; disposing at least one O-ring over the ring to make a seal between the ring and the membrane; disposing the ring with the membrane and the O-ring over the thermal block; disposing the thermal block and the ring, with the membrane and the O-ring, in an opening of the upper block; and disposing the upper block with the thermal block, the ring, the membrane, and the O-ring in the opening of the lower block such that the upper block completely closes off the opening in the upper surface of the lower block. The method can further comprise: disposing at least one end clip disposed on a corner of an outer surface of the lower block, the at least one end clip comprising a C-shaped clip; and disposing the first syringe in the C-shaped clip. The battery-operated heater can be, for example, an electronic hand-warmer. The method can further comprise: providing a second syringe and disposing a second needle on the second syringe; and coupling the second needle to a first end of a second tubing, and coupling a second end of the second tubing to the serpentine pathways of the ring. The 3D printer can be, for example, a direct drive FDM-type 3D printer, and/or the housing can comprise a thermochromic material that changes color as its temperature changes. The thermal block can comprise a cylindrically-shaped main portion and a collar portion protruding from a lower section of the main portion; the main portion of the thermal block can be disposed through an opening of the upper block; and/or the ring can be disposed circumferentially around the main portion of the thermal block.

DETAILED DESCRIPTION

Figure 1:
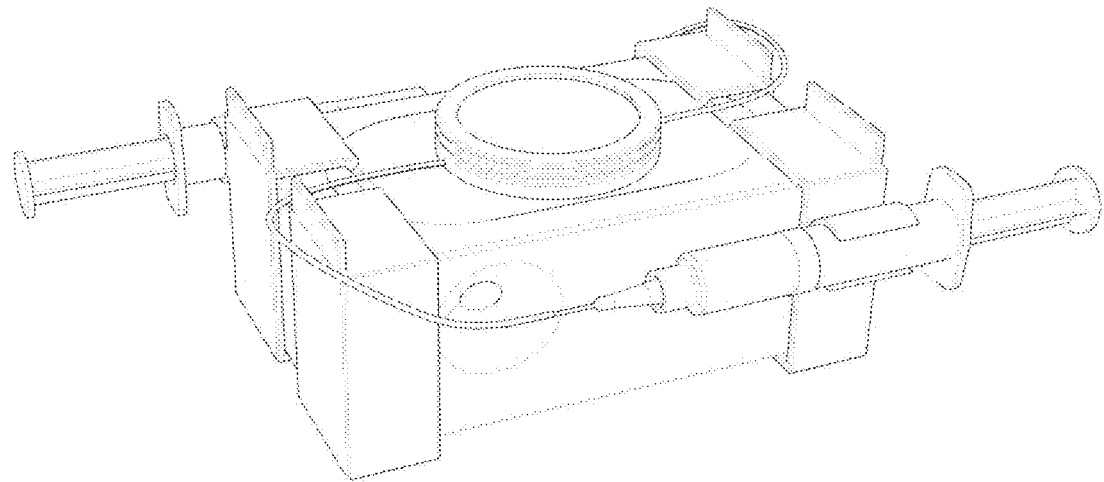
FIG. 1 is a schematic view of a blood-feeding system according to an embodiment of the subject invention.

Embodiments of the subject invention provide novel and advantageous blood-feeding systems for hematophagous arthropods, as well as methods of fabricating and using the same. The blood-feeding systems are low-cost, portable, thermally stable, and have superior blood-handling features. They can be fabricated on site (e.g., in a lab), for example by using a three-dimensional (3D) printer (e.g., a direct drive 3D printer such as a direct drive fused deposition modeling (FDM)-type 3D printer) and regular lab tools. The blood-feeding systems are the first fully portable blood-feeders that stay warm for extended periods. The systems can utilize a syringe filling system that allows leftover blood to be recovered after use, or added or changed while the feeder is in use.

In blood-feeding systems of embodiments of the subject invention, warmth can be provided by a heater (e.g., an electric heater such as an electric hand-warmer). The heater can be powered by batteries (e.g., rechargeable batteries, such as rechargeable lithium-ion batteries). Being battery-powered, the system is not tethered to a base station by wires or warm water tubes, so it can be carried to a site of use (e.g., a cage) rather than carrying the site of use (e.g., a cage) to the feeder. The system can sit blood-side down on top of a cage screen, or blood-side up either inside a cage (having hematophagous arthropods) or under the cage. The system can have a thermochromic housing (e.g., a 3D-printed thermochromic housing), and temperature can be monitored visually by observing the color of the thermochromic housing. The system can include thermal insulation (e.g., printed-in thermal insulation), which can allow it to stay warm as long as 10 hours on a single battery charge. After use the battery or batteries can recharged (e.g., using a USB cable).

Embodiments can incorporate a commercially available hand-warmer as the heat source, and this can increase reliability and significantly lower the cost compared to fabricating a rechargeable battery-powered heater from parts. Incorporating a hand-warmer also eliminates the considerable time and skills involved in wiring components to a printed circuit board and programming a microprocessor. The safety factor is much greater with an electronic hand-warmer because temperature regulation and charging of the hand-warmer are microprocessor-controlled and protected against thermal runaway. Commercially available hand-warmers are sturdy enough to resist damage from falls. These features virtually eliminate the risk of the system catching fire if it gets dropped on the floor, a significant concern with lithium-ion batteries in do-it-yourself electronics. A possible limitation of the hand-warmer is that it could be restricted to three pre-set temperatures. In one embodiment, the lowest setting of the hand-warmer can produce a blood temperature of 39° C., which mosquitoes find very attractive. Lower temperatures can be achieved, if desired, by redesigning the heat-conductor to conduct less heat to the blood surface or using a less conductive material.

Figure 2:
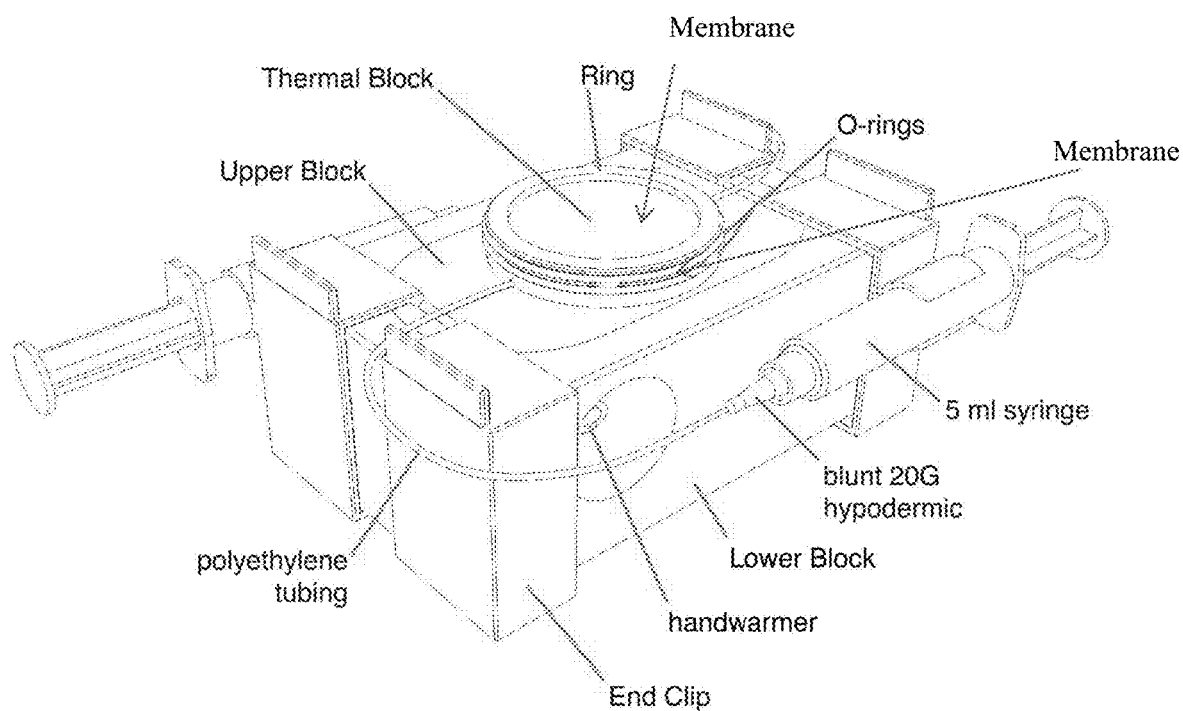
FIG. 2 is a schematic view of a blood-feeding system according to an embodiment of the subject invention.
Figure 3:
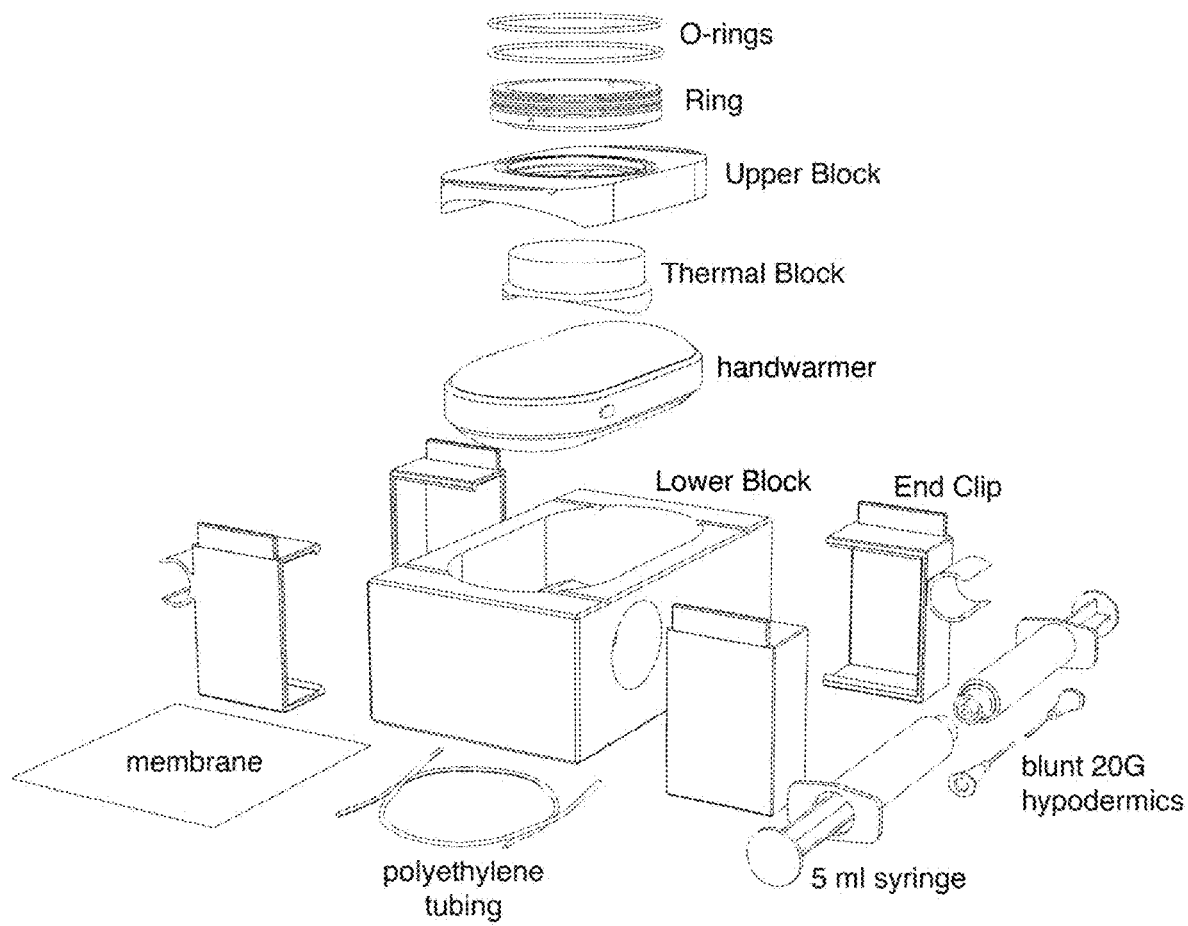
FIG. 3 is an exploded view of a blood-feeding system according to an embodiment of the subject invention.

FIGS. 1 and 2 show schematic views of a blood-feeding system according to an embodiment of the subject invention, and FIG. 3 shows an exploded view of the blood-feeding system. Referring to FIGS. 1-3, the blood-feeding system can comprise a housing including a lower block, an upper block, and a thermal block. The housing can be a thermochromic housing (e.g., a 3D-printed thermochromic housing), though embodiments are not limited thereto. The upper block can be disposed on the lower block, for example within an opening on an upper portion of the lower block, and the thermal block can be disposed on or in the upper block (e.g., within an opening or hole of the upper block). The thermal block can include a cylindrically-shaped main portion and a lateral protrusion or collar portion at a lower section of the main portion, and this collar-portion can help hold the thermal portion within the upper block after the main portion of the thermal block is inserted through the opening or hole of the upper block (see FIG. 3).

Figure 4:
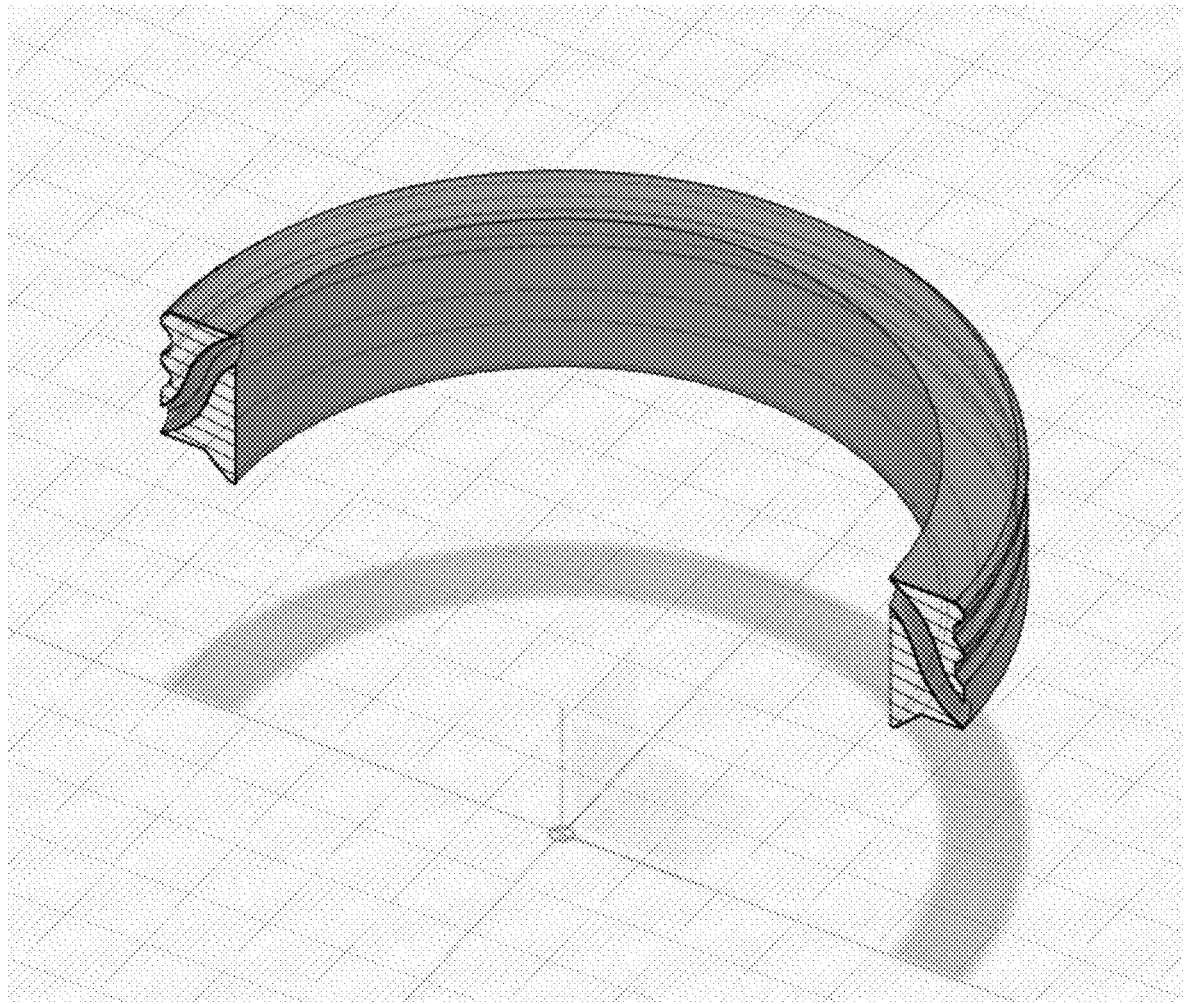
FIG. 4 is a cutaway section of a ring that can be used with a blood-feeding system according to an embodiment of the subject invention. The cutaway section was modeled in computer aided design (CAD) software and shows serpentine paths for the tubing pieces (e.g., polyethylene tubing pieces) that fill and purge the blood compartment. Tubing can exit the serpentine paths horizontally at both ends, snaking around the thermal block of the system on the inside and around the grooves for the O-rings of the system on the outside.

The system can further comprise a ring disposed on and/or around (e.g., circumferentially around) the thermal block and/or within an opening or hole of the upper block. The system can further comprise at least one O-ring coupled with the ring and making a seal (e.g., an air-tight seal) between the ring and at least one other element (e.g., the upper block, the thermal block, and/or a membrane of the system). The ring can include pathways (e.g., serpentine pathways) therewithin through which tubing can be threaded (see also FIG. 4).

The system can further comprise at least one syringe that may be disposed outside the lower block, for example on at least one respective side surface of the lower block. Each syringe can be a disposable syringe, though embodiments are not limited thereto. Each syringe can have a needle (e.g., a hypodermic needle) attached thereto, and the needle can have a tubing (e.g., a flexible tubing) attached thereto and connecting to the ring (the tubing can be threaded through pathways in the ring). Though the figures list a volume of the syringe, a size and type of the needle, and a material of the tubing, these are for exemplary purposes only and should not be construed as limiting. Any suitable size and/or material can be used for these elements. The system can further comprise a heater (e.g., an electric hand-warmer) disposed within the lower block. The heater can be fully contained within the housing (for example, by being enclosed within the housing by the upper block being disposed within the opening on the upper surface of the lower block). Though the figures indicate the heater is a hand-warmer, embodiments are not necessarily limited thereto. The system can further comprise at least one end clip (e.g., four end clips) disposed on at least one respective corner of an outer surface of the lower block. The end clip(s) can include a C-shaped clip for holding the syringe. For example, the system can include two syringes, and two end clips disposed on opposite corners of the lower block can each include a C-shaped clip for respectively holding the two syringes on opposite lateral sides of the lower block, as depicted in FIGS. 1 and 2. In an embodiment, as depicted in FIGS. 1 and 2, the system can comprise four end clips disposed on the four respective corners of the outer surface of the lower block, with two of the end clips on opposite corners including a C-shaped clip and two of the end clips on the other two corners not having a C-shaped clip but having a vertical protrusion. The vertical protrusions can be used to hold the tubing in place, as depicted in FIGS. 1 and 2.

The system can further comprise a membrane disposed on and/or around the thermal block, held in place and sealed with the ring and the O-ring(s). When fabricating the system, the membrane can be placed over the thermal block; and the ring, O-rings, and upper block can then be secured into place over the membrane and the thermal block (see also FIGS. 2 and 3). The membrane can be, for example, a collagen membrane, a Parafilm-M membrane, or an intestine sausage casing, though embodiments are not limited thereto.

At least one syringe can include blood, and the blood can be loaded from the syringe(s) to the ring or the thermal block. A second syringe can be used to remove air from a blood compartment of the system (e.g., from the ring). The system is configured to prevent or inhibit leakage during loading or operation and to eliminate or inhibit air bubbles. The syringe(s) can be sized such that the system holds an amount of blood as desired by the user for a particular use. That is, a larger syringe size can be used if more blood volume is desired, and a smaller syringe size can be used if less blood volume is desired. Unconsumed blood can be recovered for reuse, if desired. The system can accommodate any thin feeding membrane. Intestine sausage casings are preferred by mosquitoes but dry out in long feeding sessions and sometimes have holes. Collagen membranes perform like intestine sausage casings, but are more uniform. Parafilm-M casings are less appealing to mosquitoes but do not dry out. The feeding membrane can be held in place with at least one O-ring (e.g., two O-rings) for enhanced leak resistance. The system can disassemble quickly without tools, and parts can be easily cleaned (e.g., in a sink under running water).

Embodiments of the subject invention provide thermally stable, self-contained blood feeders that can be fabricated on site (e.g., in a lab), for example using a direct drive FDM-type 3D printer and regular lab tools. The system, which can be referred to as a "Pheeder", works extremely well in the lab as an arthropod blood feeder (e.g., a mosquito blood feeder or tick blood feeder), with the flexible geometry facilitating feeding of any type of hematophagous arthropod. Compared to related art blood feeders, the Pheeder has lower cost, full portability, and superior blood-handling.

The Pheeder is the least expensive of continuously heated blood-feeding systems. Excluding the cost of labor and tools, the per unit cost to produce a Pheeder can be, for example, $51 (USD) in quantities of eight, or $61 in quantities of six. By contrast, related art commercial multiplexed blood-feeding systems typically cost $1200-$2500. With access to a direct drive 3D printer, per-unit costs for the Pheeders are less than one tenth the cost of existing commercial units. Even purchasing a new 3D printer, the material costs would still be lower. The Pheeder's parts are sufficiently tough to withstand a knocks in the sink or a drop on the floor. Researchers can fabricate the Pheeder in the lab, and most universities have 3D print labs.

The Pheeder is the first fully portable blood-feeding system that stays warm for extended periods. While the classic blood-filled sausage casing is portable, it does not maintain temperature. Existing heated systems are attached to a temperature-regulating base station by hoses or electric cables. Blood in the Pheeder is kept warm by a portable heater (e.g., an electronic hand-warmer), powered by one or more batteries (e.g., rechargeable batteries, such as rechargeable lithium-ion batteries). Being battery-powered, the Pheeder is not tethered to a base station by wires or warm water tubes, so it can be carried to the site of use (e.g., a cage) rather than carrying site of use (e.g., a cage) to the Pheeder. The Pheeder is a small standalone device (e.g., for example about the size of an iPhone® box (about 80 mm×about 73 mm×about 50 mm)) that can be moved around without a base station and placed inside a cage with hematophagous arthropods. The Pheeder can sit blood-side up either inside the cage or under the cage, or blood-side down on top of the cage screen. Temperature can be monitored visually by observing the color of the Pheeder's 3D-printed thermochromic housing. The temperature can be measured using, for example, an infrared (IR) thermometer (e.g., a calibrated IR thermometer). The Pheeder can hold the fluid (e.g., blood) stable for a long period of time (e.g., at a stable 39° C. for 11 hours on a single battery charge). The battery or batteries (e.g., a lithium-ion battery) can be recharged with a cable (e.g., a USB cable).

In an embodiment, a commercially available hand-warmer can be used as the heater. Incorporating a commercially available hand-warmer into the Pheeder as its heat source increases reliability and significantly lowers the cost compared to fabricating a rechargeable battery-powered heater from parts. The safety factor is much greater with an electronic hand-warmer because temperature regulation and charging the hand-warmer are microprocessor-controlled and protected against thermal runaway. The Pheeder's printed-in thermal insulation in the lower block and upper block allow it to conserve power and stay warm for an entire day's use. Lower temperatures can be achieved, if desired, by slicing the thermal block with partial infill to conduct less heat to the blood surface or by making it from a less thermally conductive material (e.g., a less thermally conductive plastic).

In an embodiment, a charged heater (e.g., electronic hand-warmer) can be disposed into the lower block (e.g., through an opening in the upper surface thereof; the upper block can be disposed on top (e.g., in the opening of upper surface of the lower block); and the end clips can be disposed on (e.g., slipped on) the corners of the outer surface of the lower block. The membrane (e.g., an 8-centimeter (cm) diameter membrane or 8 cm×8 cm square membrane) can be placed over the ring. In order to secure the membrane on the ring, two O-rings (e.g., oil-resistant O-rings such as Oil-Resistant Buna-N O-Ring, 1.5 mm Wide, 47 mm ID, USA Sealing, Inc.) can be fit over the membrane and pressed into outer grooves in the ring.

A blunt needle can be fit on a syringe (e.g., a Luer-lock syringe), and the syringe can draw blood to fill (at least partially) the syringe and purge the syringe of air (while trying to avoid bubbling the blood). The needle on the blood-loaded syringe can be inserted into one loose end of tubing, and an extra needle on an extra syringe can optionally be inserted into another loose end of tubing. The other end of the tubing(s) can be connected to the ring or the thermal block. The Pheeder can be tipped (e.g., at about 60° on end, blood-tube down), and the blood can be injected into the blood compartment of the Pheeder (e.g., via the ring). The second (extra) syringe can be pulled back on the plunger to purge any air bubble(s) in the blood compartment. The syringes can be fit into the C-shaped clips of opposite end clips. The hand-warmer can be turned on at any point (e.g., before adding blood, while adding blood, or after adding blood). The appropriate desired setting on the hand-warmer can be set (e.g., low). The ring can have grooves for O-rings (e.g., for two O-rings), one of which can be used to hold the membrane, leaving another free (e.g., to hold in place a piece of other material (e.g., nylon stocking) with odorant for olfactory choice experiments, if desired). The Pheeder is then ready to use for feeding hematophagous arthropods. After use, the parts that contact blood should be disassembled and rinsed under running water to keep blood from adhering. While the 3D-printed parts of the Pheeder are robust, the tubing (e.g., polyethylene filling tubes) may be thin, so care should be taken to avoid kinking, stretching, or tugging them.

Embodiments of the subject invention provide the first fully portable blood-feeder that stays warm for extended periods. The Pheeder's syringe filling system allows leftover blood to be recovered after use, or added or changed while the feeder is in use. In addition, the Pheeder is less expensive than related art continuously heated blood-feeder systems, and users can fabricate it themselves. The Pheeder is a small standalone device (e.g., about 80 mm×about 73 mm×about 50 mm) that can be moved around without a base station and placed inside a cage with hematophagous arthropods. The Pheeder's parts are sufficiently tough to withstand a bumps or drops.

When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Materials and Methods

A blood-feeding system as depicted in FIGS. 1-3 was fabricated. A charged electronic hand-warmer was be disposed into the lower block through an opening in the upper surface thereof; the upper block was disposed on top (in the opening of upper surface of the lower block); and the end clips were slipped on the corners of the outer surface of the lower block. An 8-cm diameter membrane was placed over the ring. In order to secure the membrane on the ring, two O-rings (Oil-Resistant Buna-N O-Ring, 1.5 mm Wide, 47 mm ID, USA Sealing, Inc.) were fit over the membrane and pressed into outer grooves in the ring.

A blunt needle was fit on a 5-milliliter (ml) Luer-lock syringe, and the syringe was used to draw blood to fill (at least partially) the syringe and purge the syringe of air (while trying to avoid bubbling the blood). The needle on the blood-loaded syringe was inserted into one loose end of polyethylene tubing, and a second needle on a second syringe was inserted into another loose end of polyethylene tubing. The other end of each of the tubings was connected to the ring. The Pheeder was tipped at about 60° on end, blood-tube down, and the blood was injected into the blood compartment of the Pheeder (e.g., via the ring). The second syringe was pulled back on the plunger to purge any air bubble(s) in the blood compartment. The syringes were fit into the C-shaped clips of opposite end clips. The hand-warmer was turned on and set to low. Immediately after each use, the parts that contact blood were disassembled and rinsed under running water to keep blood from adhering. While the 3D-printed parts of the Pheeder are robust, the tubing (e.g., polyethylene filling tubes) may be thin, so Care was taken to avoid kinking, stretching, or tugging the polyethylene tubings.

An electronic hand-warmer that seemed to have the lowest temperature setting was used (Augola™ DELUX Rechargeable Electronic Hand Warmer, 5200 mAh 2-in-1 Double-Sided Heating Hand Warmer and Powerbank). The exact same model was available from different suppliers under different names and at different prices. It has three LEDs to indicate the temperature settings and charging status and a single control button on the side. A microUSB port allowed for charging. The Pheeder parts that were 3D-printed were modeled in CAD software.

The thermal block was 3D-printed and used to transfer heat from the hand-warmer to the blood. The shape of the electronic hand-warmer was incorporated into the model so that the thermal block makes good contact with the hand-warmer's upper surface. In order to capture the shape of the hand-warmer, a wire contour gage (General Tools 837) was pressed against the hand-warmer's upper surface. The contour of the gage wires was traced onto paper and a 10-cm line was added for scale. The drawing was scanned, imported into a vector graphics program (e.g., Adobe Illustrator or Inkscape), traced, and saved in SVG format. The SVG file was imported into a CAD file and scaled to correct size using the 10-cm line. The profile was then fitted with a fit-point spline curve in another sketch on the same plane and incorporated into the model.

The completed Pheeder was filled with blood through one length of polyethylene tubing and the air bubble purged through another. Serpentine pathways (1.6-millimeter (mm) diameter), through which the tubing was threaded, were designed into the ring that holds the Pheeder membrane (see also FIG. 4).

The blood volume is set by the thickness of the thermal block. It can be made thicker to increase blood volume or thinner to reduce blood volume, trimming notches in the flat surface to accommodate the polyethylene filling tubes. The block used for testing was adjusted to accommodate 3 ml of blood.

When the modeling was complete, the files were exported in STL format. 3D models need to be converted to gcode, a text file of instructions that guide the printer's actions. Gcode conversion was accomplished by a "slicer" program. Slicer settings for each part are provided below.

- Lower Block: material—PLA (color-changing preferred); nozzle—0.4 mm; face on bed—no change (flat side down); configuration—generic PLA; layer thickness—0.2 mm quality; infill—15%, cubic or gyroid (for insulation).
- Upper Block: material—PLA (color-changing preferred); nozzle—0.4 mm; face on bed—upside down (flat side down); configuration—generic PLA; layer thickness—0.2 mm quality; infill—15%, cubic or gyroid (for insulation).
- Ring: material—PLA (color-changing preferred); nozzle—0.4 mm; face on bed—upside down (flat side down); configuration—generic PLA; layer thickness—0.1 mm detail; infill—15%, cubic or gyroid (for insulation); seam position—align to rear.
- End Clips: material—PETG; nozzle—0.4 mm; face on bed—largest side down; configuration—generic PETG; layer thickness—0.2 mm quality; infill—100%.
- Thermal Block: material—Ice9 Flex™ TPE; nozzle—0.8 mm; face on bed—upside down (flat side down); configuration—generic FLEX, modified with settings below; layer thickness—0.4 mm quality; infill—100% rectilinear (or 95% to reduce build-up on nozzle); seam position—align to rear.
- Speed: perimeters—30 millimeters per second (mm/s); small perimeters—20 mm/s; external perimeters—20 mm/s; infill—40 mm/s; top solid infill—30 mm/s; acceleration control—200 mm/s (all accel. settings); max print speed—40 mm/s.
- Extrusion Width: default extrusion width—0.9 mm; first layer—0.84 mm; perimeters—0.9 mm; external perimeters—0.9 mm; infill—0.9 mm; solid infill—0.9 mm; top solid infill—0.8 mm; slice gap closing radius—0.098 mm; nozzle width—0.8 mm.

The upper and lower blocks were sliced at 0.2 mm layer height, with a partial infill (15%) to incorporate air cells that act as insulation, preventing or inhibiting the outsides of the heater from getting warm. Absent sufficient insulation, mosquitoes are drawn to the housing in addition to the blood compartment. The ring was sliced at a finer 0.1 mm layer height to keep the serpentine tunnels smooth.

The thermal block was printed from a special thermally-conductive flexible filament (Ice9 Flex™, TCPoly, Inc.). It started with a generic flex slicer profile and then was modified using print settings recommended by the manufacturer, including a 0.8 mm print nozzle because smaller nozzles will clog. Layer height was be set to 0.4 mm. In order to reduce filament build-up on the print nozzle, infill density was set at 95%.

The models were printed on an FDM 3D printer. The upper and lower housing blocks and the ring were printed from polylactic acid (PLA) using a 0.4 mm nozzle. PLA is a plant-derived plastic that prints well but tends toward the brittle side. While any PLA filament would have been acceptable, a thermochromic PLA with a low temperature threshold was used, allowing users to gauge the temperature of the blood compartment by the color of the adjacent PLA parts (Zi-Rui Tri Color Changing with Temperature, Pine Green to Light Orange to Yellow). If a thermochromic PLA is used, chilling the printed parts in the freezer one time quickly resets the thermochromic dye from the extreme heat of printing.

The end clips were printed from a more flexible plastic, PETG, which allowed the syringe holders to flex without breaking. Ice9 Flex™ filament, from which the thermal block was printed, conducts heat from the hand-warmer to the blood as efficiently as steel. Printing with any flexible filament requires a printer with a direct drive extruder, such as the Prusa MK3 S. The cheaper and more common Bowden drive printers, including the Prusa Mini, work well for every other part printed in PLA and PETG, but can't handle flexible filaments. The drive gears of a Bowden drive mechanism push the filament through a long Teflon tube into the printer's hot end and nozzle. As a result, flexible filament in a Bowden drive behaves like a strand of cooked spaghetti and bunches up. A direct drive printer has the drive gears directly above the heater block, pulling the filament over most of its free length rather than pushing it.

Flex filaments are hydroscopic. A filament that has absorbed moisture from the air will not print properly. Even with a new roll of flexible filament, it's best to bake the spool for several hours at 70° C. before printing (the PrintDry™ system, a modified food dryer, was used for this). The spool was stored in a dry bag with silica desiccant. PLA and PETG filaments were likewise be stored dry, though, unlike TPE flex filaments, they rarely need to be baked dry prior to first use (although it may happen).

In order to print Ice9 Flex, the 0.4 mm nozzle was changed out and replaced with a 0.8 mm nozzle (purchased separately). The print bed was covered with a layer of blue painter's masking tape from which the print was easily removed. The first layer height was recalibrated to accommodate for the nozzle change and thickness of the tape.

Ice9 Flex filament has some atypical properties. It adheres to the printer's hot metal parts like bubblegum on hot asphalt, even worse than PETG, so a small brass wire brush is essential for cleaning the print nozzle after a print (the hot end can be re-heated if necessary). A silicone protective sock should not be used on the hot end—Ice9 will find its way underneath causing bigger problems. When Ice9 printing is complete, a series of "cold pulls" were performed with the 0.8 mm nozzle in place to clean all the Ice9 from the inside of the extruder. If the cold pulls are not performed, the printer will have clogs and random streaks of Ice9 will appear in future prints. Ice9 Flex resembles molten lead in its heat retention; a small blob of Ice9 Flex dripping onto the print bed from the print nozzle can burn one's fingers long after every other plastic would be safe to touch.

Blood was injected into the Pheeder through polyethylene tubing (Intramedic™ PE Tubing, OD 0.050 inches (in)/0.86 mm). This diameter tubing is fit perfectly by 20G hypodermic needles, which is what was used for the testing. The needles were blunt to avoid puncturing the tubing. Blunt 20

G hypodermic needles can be purchased or made by grinding the tips off sharp 20 G hypodermic needles (e.g., with a Dremel hand grinder). The needle shaft was about 25 mm (1 in) in length.

The contoured surfaces of the thermal block and the upper block were aligned, and the tube holes in the ring were aligned along the long axis of the upper block. Then, the thermal block was pressed through the upper block onto the ring. The three parts hold together snugly. If the alignment is not perfect when performing this alignment, it can be disassembled and redone.

Two 15-cm lengths of polyethylene capillary tubing were cut and threaded into the serpentine tunnels in the ring. The ends extended inside the ring by 7 mm to 10 mm. The tubing ends inside the ring were blocked with toothpicks or tape to keep epoxy out. Clear epoxy (4.5 ml; Smooth-On™ XTC-3D High Performance 3D Print Coating) was mixed. Disposable 3-ml syringes were used to get the proportions of Part A and Part B exactly 2:1. Using a 1-in foam brush, epoxy was applied to the flat blood surface of the thermal block and the inside of the ring. The epoxy coat was brushed and re-brushed to coat evenly and eliminate bubbles, and then was allowed to sit while the epoxy leveled and set. The next day when the epoxy was hard, the assembly was placed under a dissecting microscope and, using a scalpel, the tubes were trimmed to be flush with the inside of the ring. If you a mess is made in this step, the ring can be cut free after the epoxy hardens and the thermal block salvaged by sanding the epoxy flat (another ring can be printed from PLA to try again). If more than one Pheeder is being fabricated, a pourable silicone rubber (e.g., Sylgard™) could serve as a good substitute for the clear epoxy because it takes longer to set, allowing the bubbles to be sucked out under vacuum.

Example 1

The Pheeder was tested against a blown-glass feeder heated with water. The day before the trial, 15-day-old female *Aedes aegypti* mosquitoes of the Orlando strain were placed in cages (BugDorm™), 50 to a cage, with deionized water available to drink, but no sucrose. Three feeder setups were compared. Feeder 1 was a blown-glass feeder, warmed with pumped water at 36.5° C., with a membrane of Parafilm-M. Feeder 2 was a Pheeder set to the lowest heat setting, also with a membrane of Parafilm-M. Feeder 3 was a Pheeder set to the lowest heat setting, with a water-soaked collagen membrane (LEM Products™ Fresh Clear Edible Collagen Casing). While the feeders warmed up, each feeder was fit with its membrane and filled with 3 ml of defibrinated sheep's blood, spiked with adenosine triphosphate (ATP). No carbon dioxide ($CO_2$) supplement was used to stimulate feeding. The cages were placed on their sides so the top surface was screened, and feeders were placed in the inverted position on top of the cage. For the next 30 minutes, the feeders and cages were visually inspected every five minutes to count mosquitoes on the feeder membrane and to count engorged mosquitoes that had left the membrane. At 40 minutes, the feeders were removed, and both engorged and unfed mosquitoes were counted twice, inspecting the cages from all angles. A few engorged mosquitoes had remained on the glass feeder's membrane after feeding and thus were not counted as engorged until the feeders were removed. Membrane temperature was measured by a National Institute of Standards and Technology (NIST)-calibrated infrared thermometer (Fluke™ model 62) set to an emissivity of 0.98, which proved accurate in previous cross-calibration tests using heated water and the two membrane types.

Figure 5:
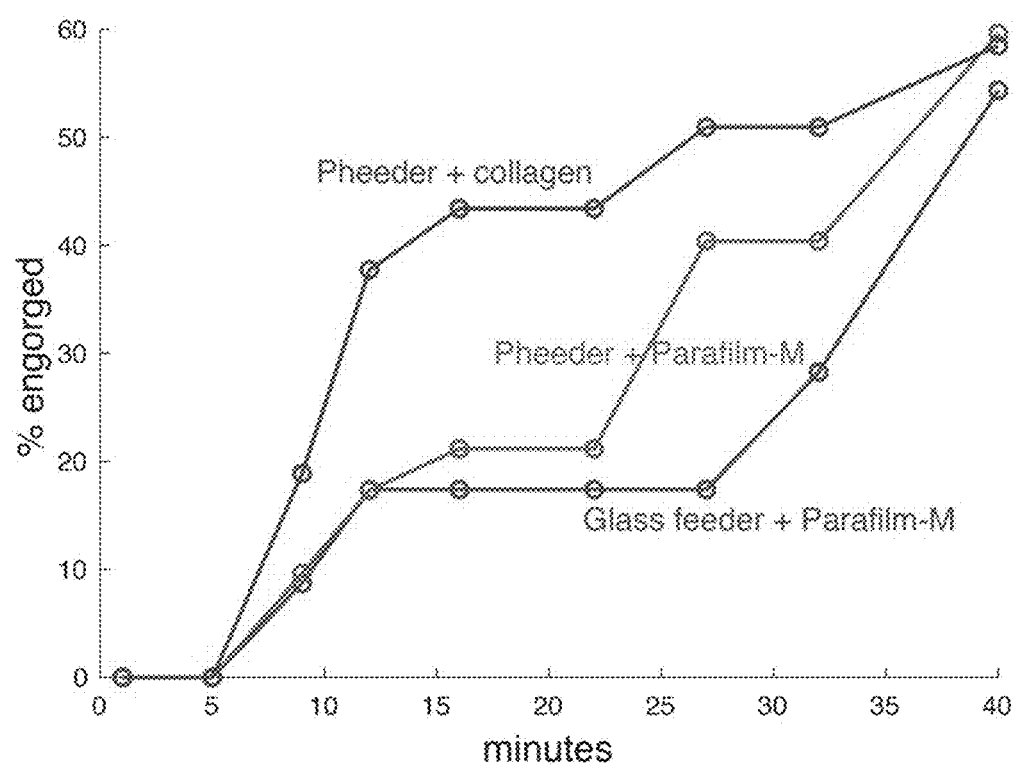
FIG. 5 is a plot of percentage of adult female *Aedes aegypti* mosquitoes that were engorged versus time (in minutes), comparing a system of an embodiment of the subject invention (referred to in FIG. 5 as a "Pheeder") to a water-heated blown-glass feeder. The (green) curve with the highest % engorged value at 15 minutes is for the Pheeder with a collagen membrane; the (red) curve with the second-highest % engorged at 15 minutes is for the Pheeder with a Parafilm-M membrane; and the (blue) curve with the lowest % engorged at 15 minutes is for the water-heated blown-glass feeder with a Parafilm-M membrane. The Pheeder with a collagen membrane had a higher percentage of engorged adult female mosquitoes for at least the first 15-20 minutes, with the Pheeder with the Parafilm-M having the next highest percentage engorged and the glass feeder having the lowest percentage. The Pheeder with the Parafilm-M membrane caught up to the Pheeder with the collage membrane after 40 total minutes, while the glass feeder with the Parafilm-M membrane nearly caught up to the Pheeder with the collagen membrane after 40 total minutes but still had the lowest percentage engorged. The flat spot in the glass feeder curve may have resulted from some engorged mosquitoes resting on the membrane where they were scored as feeding rather than engorged until the feeders were removed at 40 minutes.

The results are shown in FIG. 5, which is a plot of percentage of engorged mosquitoes versus time (in minutes). Referring to FIG. 5, all three feeders produced similar levels of blood-engorged females after 40 minutes—54% for the blown-glass feeder (Feeder 1) and 60% and 58%, respectively, for Feeders 2 and 3. In the first 15 minutes, the collagen membrane fed twice as many mosquitoes as the Parafilm-M membranes, but the two feeders with Parafilm-M membranes caught up after 40 minutes. Ending temperatures measured on the membrane by infrared emissivity were 34.1° C. (blown-glass with the Parafilm-M membrane), 36.8° C. (Pheeder with the Parafilm-M membrane), and 30.1° C. (Pheeder with the collagen membrane). Evaporation from the collagen membrane cooled the blood surface, and the collagen had dried out noticeably after 40 minutes.

The Pheeders produced engorgement numbers at least as good as the blown-glass feeder. The Pheeder has lower cost, is portable, is versatile in blood-handling, and can accommodate multiple membrane types. The blown-glass feeders are a little quicker to set up and clean. Compared to Parafilm-M, a collagen membrane is faster for feeding mosquito lab strains but dries out if a feeding session lasts longer than 20 minutes, as might be the case with field strains that have not been selected to feed on something other than a live mammal.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A blood-feeding system for hematophagous arthropods, the system comprising:
    a housing comprising a lower block having an opening in an upper surface of the lower block, an upper block disposed in the opening the upper surface of the lower block, and a thermal block disposed on or in the upper block;
    a battery-operated heater disposed in the lower block;
    a ring disposed on the thermal block;
    a first syringe connected to the ring via a first tubing, the first syringe configured to provide blood to the ring via the first tubing; and
    a membrane disposed on the thermal block.

2. The system according to claim 1, the ring comprising serpentine pathways through which the first tubing is threaded.

3. The system according to claim 1, further comprising at least one end clip disposed on a corner of an outer surface of the lower block,
    the at least one end clip comprising a C-shaped clip into which the first syringe is disposed.

4. The system according to claim 1, further comprising at least one O-ring coupled with the ring and making a seal between the ring and the membrane.

5. The system according to claim 1, the battery-operated heater being an electronic hand-warmer.

6. The system according to claim 1, further comprising a second syringe connected to the ring via a second tubing, the second syringe configured to remove air from the ring via the second tubing.

7. The system according to claim 6, further comprising a first end clip disposed on a first corner of an outer surface of the lower block and a second end clip disposed on a second corner of the outer surface of the lower block,
the first end clip comprising a first C-shaped clip into which the first syringe is disposed, and
the second end clip comprising a second C-shaped clip into which the second syringe is disposed.

8. The system according to claim 1, the first syringe comprising a blunt hypodermic needle, via which the first syringe is coupled to the first tubing.

9. The system according to claim 1, the housing comprising a 3D-printed thermochromic material that changes color as its temperature changes.

10. The system according to claim 1, the upper block completely closing off the opening in the upper surface of the lower block,
the thermal block comprising a cylindrically-shaped main portion and a collar portion protruding from a lower section of the main portion,
the main portion of the thermal block being disposed through an opening of the upper block, and
the ring being disposed circumferentially around the main portion of the thermal block.

11. A method of providing blood to feed hematophagous arthropods, the method comprising:
providing the blood-feeding system according to claim 1;
turning on the battery-operated heater and allowing the housing to reach a predetermined temperature;
filling the first syringe at least partially with the blood;
pushing a first plunger of the first syringe to provide blood to the ring via the first tubing; and
placing the blood-feeding system with the blood provided to the ring on a container having the hematophagous arthropods.

12. The method according to claim 11, the housing comprising a 3D-printed thermochromic material that changes color as a temperature of the housing changes, and
the method further comprising monitoring the temperature of the housing based on the color of the 3D-printed thermochromic material.

13. The method according to claim 11, the system further comprising a second syringe connected to the ring via a second tubing, the second syringe configured to remove air from the ring via the second tubing, and
the method further comprising, prior to placing the blood-feeding system with the blood provided to the ring on the container, pulling a second plunger of the second syringe to remove air from the ring via the second tubing.

14. A method of fabricating a blood-feeding system for hematophagous arthropods, the method comprising:
utilizing a 3D printer to print a housing comprising a lower block having an opening in an upper surface thereof, an upper block configured to be disposed in the opening of the lower block, and a thermal block configured to be disposed on or in the upper block;
utilizing the 3D printer to print a ring comprising serpentine pathways therewithin;
disposing a battery-operated heater in the lower block of the housing through the opening of the lower block;
providing a first syringe and disposing a first needle on the first syringe;
coupling the first needle to a first end of a first tubing, and coupling a second end of the first tubing to the serpentine pathways of the ring;
disposing a membrane over the ring;
disposing at least one O-ring over the ring to make a seal between the ring and the membrane;
disposing the ring with the membrane and the O-ring over the thermal block;
disposing the thermal block and the ring, with the membrane and the O-ring, in an opening of the upper block; and
disposing the upper block with the thermal block, the ring, the membrane, and the O-ring in the opening of the lower block such that the upper block completely closes off the opening in the upper surface of the lower block.

15. The method according to claim 14, further comprising:
disposing at least one end clip disposed on a corner of an outer surface of the lower block, the at least one end clip comprising a C-shaped clip; and
disposing the first syringe in the C-shaped clip.

16. The method according to claim 14, the battery-operated heater being an electronic hand-warmer.

17. The method according to claim 14, further comprising:
providing a second syringe and disposing a second needle on the second syringe; and
coupling the second needle to a first end of a second tubing, and coupling a second end of the second tubing to the serpentine pathways of the ring.

18. The method according to claim 14, the 3D printer being a direct drive fused deposition modeling (FDM)-type 3D printer, and
the housing comprising a thermochromic material that changes color as its temperature changes.

19. The method according to claim 14, the thermal block comprising a cylindrically-shaped main portion and a collar portion protruding from a lower section of the main portion,
the main portion of the thermal block being disposed through an opening of the upper block, and
the ring being disposed circumferentially around the main portion of the thermal block.

20. A blood-feeding system for hematophagous arthropods, the system comprising:
a housing comprising a lower block having an opening in an upper surface thereof, an upper block disposed in the opening of the lower block, and a thermal block disposed on or in the upper block;
a battery-operated electronic hand-warmer disposed in the lower block;
a ring disposed on the thermal block;
a first syringe connected to the ring via a first tubing, the first syringe configured to provide blood to the ring via the first tubing;
a second syringe connected to the ring via a second tubing, the second syringe configured to remove air from the ring via the second tubing;
a membrane disposed on the thermal block;
at least one O-ring coupled with the ring and making a seal between the ring and the membrane;
a first end clip disposed on a first corner of an outer surface of the lower block; and
a second end clip disposed on a second corner of the outer surface of the lower block, the second corner being opposite from the first corner, the first end clip comprising a first C-shaped clip into which the first syringe is disposed, the second end clip comprising a second C-shaped clip into which the second syringe is disposed the ring comprising serpentine pathways through which the first tubing is threaded, the first syringe comprising a first blunt hypodermic needle, via which the first syringe is coupled to the first tubing, the second syringe comprising a second blunt hypodermic needle, via which the second syringe is coupled to the second tubing, the housing comprising a 3D-printed thermochromic material that changes color as its temperature changes, the upper block completely closing off the opening in the upper surface of the lower block, the thermal block comprising a cylindrically-shaped main portion and a collar portion protruding from a lower section of the main portion, the main portion of the thermal block being disposed through an opening of the upper block, and the ring being disposed circumferentially around the main portion of the thermal block.

* * * * *